United States Patent [19]
Rauchschwalbe et al.

[11] Patent Number: 6,002,041
[45] Date of Patent: Dec. 14, 1999

[54] PROCESS FOR PREPARING DI-$C_1$-$C_4$-ALKYL 5-NITRO-ISOPHTHALATES

[75] Inventors: Günter Rauchschwalbe, Leverkusen; Bernhard Beitzke, Rösrath; Helmut Fiege, Leverkusen, all of Germany

[73] Assignee: Bayer Aktiengesellschaft, Leverkusen, Germany

[21] Appl. No.: 09/073,485

[22] Filed: May 6, 1998

[30] Foreign Application Priority Data

May 21, 1997 [DE] Germany .................. 197 21 221

[51] Int. Cl.⁶ .................................................. C07C 205/00
[52] U.S. Cl. .................................................. 560/20
[58] Field of Search .................................. 560/20

[56] References Cited

U.S. PATENT DOCUMENTS 2,680,730  6/1954  Martin .
5,744,628  4/1998  Pfirmann et al. .

FOREIGN PATENT DOCUMENTS

0757028 A1  7/1996  European Pat. Off. .
3335312     6/1985  Germany .

OTHER PUBLICATIONS

Laboratory technique in organic chemistry, pp. 195–196, in paricular paragraphs 166–168, 1938.

Clinton, R. O. and S.C. Laskowski. (Sep. 1948) "The Preparation of Methyl Esters" Journal of the American Chemical Society, vol. 70, No. 9, pp. 3135–3136; published in US.

Hiroshi, Takimoto. (Jan. 28, 1985) "Production of P–Nitrobenzoic Acid Ester" Patent Abstracts of Japan, European Patent Office, vol. 9, No. 130, one page, published in EPO.

Wohl, A. (1910). "Über Estersäuren un Amidsäurenden Isophthalsäure–Reihe, ein Beitrag zur Frage der Gleichwertigkelt der Stellungen 2 und 6 am Benzolkern." Ber., vol. 43, pp. 3474–3489, published in Germany. In German.

Wohl, A. (1910). "Über Estersäuren der Isophthalsäure–Reihe, ein Beitrag zur Frage der Gleichwertigkeit der Stellungen 2 und 6 am Benzolkern." Ber., vol. 43, pp. 3474–3481. In German.

Clendinning, R. A., and W. H. Rauscher. (Aug. 1961). "Synthesis of Some Substituted Alkyl Derivatives of Phthalic and Isophthalic Acids." Journal of Organic Chemistry. vol. 26, pp. 2963–2965.

Cassebaum, H. and K. Dierbach. (1996). "Dünnflüssige trijodierte Röntgenkontrastmittel für die Angiographie." Pharmasie. vol. 21(3), pp. 167–170. In German.

Singh, G.B. and H.G.S. Rathore. (Nov./Dec. 1980). "Study on Radiopaque Iothalamic Acid–A comparative evaluation of its synthesis." Indian Drugs & Pharmaceutical Industry. pp. 35–38, 38A and 38B.

*Primary Examiner*—Samuel Barts
*Attorney, Agent, or Firm*—Brinks Hofer Gilson & Lione

[57] ABSTRACT

Particularly pure di-$C_1$–$C_4$-alkyl 5-nitro-isophthalates are obtained in good yield and in a simple process by dissolving 5-nitro-isophthalic acid in a mixture of a $C_1$–$C_4$-alkyl alcohol and a solvent which is miscible or only partially miscible with water, heating in the presence of a strong acid, thus forming a second, aqueous phase, crystallizing out, after the esterification reaction has ended, the di-$C_1$–$C_4$-alkyl 5-nitro-isophthalate formed from the organic phase by cooling and removing the aqueous phase before or after the di-$C_1$–$C_4$-alkyl 5-nitro-isophthalate is separated off.

12 Claims, No Drawings

PROCESS FOR PREPARING DI-$C_1$-$C_4$-ALKYL 5-NITRO-ISOPHTHALATES

BACKGROUND OF THE INVENTION

1. Field of the Invention

Dimethyl 5-nitro-isophthalate is an important intermediate for preparing radiopaque media for intravenous administration which comprise, as X-ray-absorbing component, derivatives of 5-amino-2,4,6-triiodo-isophthalic acid. Other dialkyl 5-nitro-isophthalates may be used similarly. There is a considerable demand for such intermediates which should be obtainable at the lowest possible cost and, at the same time, in high purities. In the pharmaceutical sector, even intermediates have to be at least 99.5% pure with respect to by-products, and a particular by-product may generally be present at the most at 0.3%.

2. Discussion of the Background

A plurality of synthetic routes for preparing dimethyl 5-nitro-isophthalates are already known; however, none of them is satisfactory. According to J. Org. Chem. 26, 2963 (1961) and U.S. Pat. No. 2,680,730, dimethyl isophthalate is dissolved in concentrated or fuming sulfuric acid and nitrated using a mixture of sulfuric acid and nitric acid. The desired compound is obtained as main component; however, during the nitration (as has been found by our own experiments), not insignificant amounts of the undesirable isomeric dimethyl 4-nitro-isophthalate are formed. Additionally, variable amounts of monomethyl 5-nitro-isophthalate are formed by hydrolysis during work-up when the reaction mixture is discharged onto ice (see Example 9). The resulting product is by no means pure enough for the above-mentioned use in pharmaceutics. The product has to be purified by recrystallization, and considerable losses of yield occur. The above-mentioned literature states that the desired product is obtained in a yield of only 42% of theory. Even the recrystallized product is not yet sufficiently pure, as becomes evident when the melting point of this product (119–121° C.) is compared with the melting point of the pure product (123° C.).

According to Ber. 43, 3474 (1910) and Pharmazie, 21 (3), 167–170 (1966), dimethyl 5-nitro-isophthalate can also be obtained by esterifyng 5-nitro-isophthalic acid with a large excess of methanol (for example 33 mole of methanol/mole of 5-nitro-isophthalic acid) in the presence of sulfuric acid. In this reaction, initially the monomethyl ester and then from this the dimethyl ester is formed, which crystallizes out from the solution. However, the product which is obtained is not pure enough for pharmaceutical applications, since it comprises 0.3 to 0.5% of the monomethyl ester. Here, the product likewise has to be purified by recrystallization and the above-mentioned disadvantages have to be accepted.

The esterification of 5-nitro-isophthalic acid with diazomethane (see Indian Drugs & Pharmaceutical Industry, November/December 1980, p. 35 ff.) is also not satisfactory, since diazomethane is very toxic and carcinogenic and, owing to its high instability, can only be handled on an industrial scale if very costly safety measures are taken. A diazomethane-based production process can therefore not be carried out economically. Thus, it is not surprising that the same authors describe, in the same publication, a further process where 5-nitro-isophthalic acid is initially converted, using thionyl chloride, into its acid chloride which, after intermediate isolation, is reacted with methanol to give the desired ester. To this end, large excesses of reagents have to be employed. Moreover, very long reaction times are required (for example 48 h just for forming the acid chloride). The resulting product is not pure, and once again, it has to be purified by recrystallization, with the above-mentioned disadvantages, so that altogether three process steps are required. This complicated synthesis likewise gives the desired product in only unsatisfactory yield. Likewise, this process does not allow an economical preparation of the desired product. Another known process for the esterification of carboxylic acids is the esterification by means of dialkyl sulfate. According to the more recent prior art (EP-A 757 028), the esterification is carried out in the presence of a water-insoluble tertiary amine and water, if appropriate in the presence of a water-insoluble solvent, with addition of a base at a pH of 5 to 12. A disadvantage of this process is the use of extremely carcinogenic dialkyl sulfates. Apparently, it is not possible to prepare dimethyl 5-nitro-isophthalates in this manner. This may be due to the fact that, according to the EP-A, the resulting esters are generally worked up by distillation (in which see p. 3, line 19), which is not possible for dimethyl 5-nitro-isophthalate since even its melting point is high (123° C.) and nitro compounds do not withstand considerable thermal stress.

SUMMARY OF THE INVENTION

Surprisingly, we have now found a process which permits the preparation of di-$C_1$–$C_4$-alkyl 5-nitro-isophthalates from 5-nitro-isophthalic acid where the desired product is obtained in a single synthesis step in good yield and good space-time yield in a purity of 99.9% and more, suitable for pharmaceutical purposes.

DESCRIPTION OF THE INVENTION

The process according to the invention for preparing di-$C_1$–$C_4$-alkyl 5-nitro-isophthalates is characterized in that 5-nitro-isophthalic acid is dissolved or suspended in a mixture of a $C_1$–$C_4$-alkyl alcohol and a solvent which is immiscible or only partly miscible with water, heated in the presence of a strong acid, thus forming a second, aqueous phase, the di-$C_1$–$C_4$-alkyl 5-nitro-isophthalate formed is, after the esterification reaction has ended, crystallized out from the organic phase by cooling and the aqueous phase is removed before or after the di-$C_1$–$C_4$-alkyl 5-nitro-isophthalate is separated off If appropriate, the aqueous phase can be neutralized and/or diluted prior to its removal and/or the organic phase can be purified by extraction prior to cooling for crystallizing di-$C_1$–$C_4$-alkyl 5-nitro-isophthalates.

Preferred for use as $C_1$–$C_4$-alkyl alcohols are methanol or ethanol. For example, 3 to 8 mol of a $C_1$–$C_4$-alkyl alcohol can be employed, based on 1 mol of 5-nitro-isophthalic acid.

Suitable water-immiscible or only partially water-miscible solvents are nonpolar and slightly polar aprotic solvents, for example aromatic hydrocarbons, chloroaromatics and aliphatic ethers such as benzene, toluene, ethylbenzene, cumene, trimethylbenzenes, monochlorobenzene, mixtures of isomeric dichlorobenzenes and dibutyl ethers. Preference is given to toluene and xylene. For example, 0.2 to 5 parts by volume of a water-immiscible or only partially water-miscible solvent can be employed, based on one part by volume of $C_1$–$C_4$-alkyl alcohol.

In a particular embodiment of the process according to the invention, the 5-nitro-isophthalic acid is employed in water-moist form, if appropriate containing other acids, together with an aromatic hydrocarbon, and the water introduced is removed prior to the addition of the $C_1$–$C_4$-alkyl alcohol by azeotropic distillation, together with some of the aromatic hydrocarbon.

Suitable strong acids are, for example, sulfuric acid, hydrogen chloride (as a gas and as an aqueous solution), methanesulfonic acid, toluenesulfonic acid and ion exchangers containing $HSO_3$ groups. Preference is given to sulfuric acid and hydrochloric acid. For example, 1 to 200% by weight of strong acid can be employed, based on 5-nitro-isophthalic acid. Preferably, this amount is 10 to 100% by weight, in particular 30 to 70% by weight.

The heating in the presence of a strong acid can be carried out, for example, to temperatures in the range from 50 to 150° C. Preference is given to temperatures in the range from 70 to 110° C., in particular in the range from 80 to 100° C. Reaction temperatures which are too low result in very long reaction times; additionally, there is also the risk that the di-$C_1$–$C_4$-alkyl 5-nitro-isophthalate formed begins to crystallize out too early.

Depending on the composition of the reaction mixture, the reaction can be carried out, for example, at atmospheric pressure, if appropriate at reflux temperature, or in closed vessels under elevated pressure.

The esterification is generally complete after a reaction time of 2 to 20 hours. Preferably, this time is 3 to 10 hours. Before or after the removal of the aqueous phase and prior to cooling the prepared diester for crystallization, one or more of the following steps can be carried out, if appropriate:

filtration, for example to remove solid components (for example acid ion exchangers), removal of a sludge phase (if present) and/or clarification of the reaction mixture (using an adsorbent such as activated carbon).

If sufficiently pure 5-nitro-isophthalic acid is employed and the reaction is carried out without acid ion exchangers, an in-specification diester is obtained even without these treatment steps.

If the formation of the di-$C_1$–$C_4$-alkyl 5-nitro-isophthalate has not gone to completion, the reaction mixture which is present after the reaction contains still unreacted 5-nitro-isophthalic acid and/or its mono-$C_1$–$C_4$-alkyl ester. It is possible to prevent these from precipitating together with the desired diester by treating the entire reaction mixture or just the organic phase, if appropriate after washing with water, with an aqueous solution of a base. The phase separation required and the washes are expediently carried out at a temperature at which the di-$C_1$–$C_4$-alkyl 5-nitro-isophthalate prepared does not yet crystallize out. The base can be, for example, an alkali metal carbonate, alkali metal bicarbonate or alkali metal hydroxide. Preference is given to aqueous 5 to 20% strength by weight solutions of sodium carbonate or potassium carbonate. The substances which have been removed can, if appropriate, be recycled from the aqueous solution of a base and added to a subsequent reaction. In this manner, it is possible to increase the yield. Moreover, it is a particular advantage of the process according to the invention that a product of high purity can be obtained even at incomplete conversion. Cooling of the organic phase for crystallization can be carried out for example to temperatures between 25 and 0° C. It is advantageous to stir the organic phase during crystallization. It is generally not necessary to add seed crystals.

The process can also be carried out by not trying to precipitate the prepared diester completely during crystallization, but cooling the organic phase, for example, only to 20 to 25° C. and then adding the mother liquor to a subsequent reaction. This can result in increases in yield.

The product which has been separated off from the mother liquor after crystallization generally contains small proportions of the organic solvent employed. The product can be used in this form. If desired, the solvent-containing product can also be washed, for example with ethanol and then water, and, if appropriate, dried. The product can also be used in water-moist form.

The process according to the invention can be carried out, for example, in the following manner. 5-nitro-isophthalic acid is dissolved with heating in a mixture of the $C_1$–$C_4$-alkyl alcohol used and a nonpolar or slightly polar, aprotic solvent, and heated in the presence of a strong acid for several hours. A stoichiometric amount of water is formed. Owing to this, the solution, which is initially homogenous, separates into two phases. One phase contains predominantly water and part of the strong acid and the $C_1$–$C_4$-alkyl alcohol, the other phase contains, in addition to the organic solvent, the remainder of the $C_1$–$C_4$-alkyl alcohol, if appropriate 5-nitro-isophthalic acid and if appropriate mono-$C_1$–$C_4$-alkyl ester and necessarily the dialkyl ester formed. By the phase separation, the water of reaction is removed from the phase containing the desired main product, and it therefore cannot slow down the reaction rate and the conversion via the esterification equilibrium. After the desired reaction time, the phases are allowed to separate, the aqueous phase is removed (if appropriate after prior neutralization), the organic phase, which is still warm, may be washed free of remaining acid using basic aqueous compounds, and the desired product can then be crystallized out by cooling.

In another work-up method, the reacted reaction mixture is poured onto water containing sufficient inorganic or organic base to partially or completely neutralize the acid, and the organic phase is cooled. The heat of neutralization which is liberated may be led off by cooling. The resulting product can then be isolated by filtration. It is also possible to neutralize the acid aqueous phase, to add some additional base (for example soda or sodium bicarbonate), to cool the mixture and to separate the two liquid phases simultaneously from the solid phase by filtration. The solid phase is then the desired product.

It is also possible to choose other embodiments for the process according to the invention.

The main advantage of the process according to the invention consists in the fact that the product is obtained in one step in high yield and in the desired purity and that intermediate isolations and/or recrystallizations are not required. Compared to the prior art, the space-time yield is considerably increased. There is no need to handle highly carcinogenic substances or to add water-insoluble bases. Moreover, during the reaction the pH neither has to be controlled nor readjusted. The corresponding equipment can therefore be dispensed with.

EXAMPLES

Example 1

120 ml of methanol and 240 ml of toluene were mixed, 106 g of 5-nitro-isophthalic acid were added and the mixture was heated until a clear solution had formed. 33 ml of 100% strength sulfuric acid were added dropwise, resulting in a two-phase mixture. The mixture was heated at boiling point for 4 hours. The stirrer was then stopped, the lower (aqueous) phase was discharged and the organic phase was washed once with 100 ml of hot water and then once with 100 ml of hot 10% strength sodium bicarbonate solution. The washed organic phase was then stirred until it had cooled to room temperature. During this, dimethyl-5-nitro-isophthalate crystallized out in white crystals. The crystals were filtered off and washed once with 100 ml of methanol and once with 100 ml of water. After drying, 100 g of dimethyl 5-nitro-isophthalate (mp.: 123° C.) were obtained which, according to HPLC, were virtually 100% pure; at any rate, by-products having a content of over 0.1% by weight were not found.

Example 2

Example 1 was repeated, but the suspension of the diester was cooled to 0° C. In this manner, 100 g of pure dimethyl 5-nitro-isophthalate were isolated.

Example 3

Example 1 was repeated, but the mother liquor of Example 1 was used instead of toluene and fresh toluene was added to give the same initial charge as in Example 1. This gave 113 g of pure dimethyl 5-nitro-isophthalate.

Example 4

Example 1 was repeated, but 120 g of ethanol were employed instead of methanol. 85 g of pure diethyl 5-nitro-isophthalate were isolated, having the melting point of 83.5° C. known from the literature (see Beilstein 9,840).

Example 5

Example 1 was repeated, but xylene (technical grade) was used instead of toluene. 97.5 g of pure dimethyl 5-nitro-isophthalate were isolated.

Example 6

Example 1 was repeated, but chlorobenzene was employed instead of toluene. Phase behavior during the esterification changed in such a manner that the aqueous phase to be removed was lighter than the organic phase containing the diester prepared. 93.5 g of pure dimethyl 5-nitro-isophthalate were isolated.

Example 7

210 g of di-isobutyl ether and 19 g of methanol were initially charged, 21 g of 5-nitro-isophthalic acid were dissolved therein with heating and 7 ml of concentrated sulfuric acid were added dropwise with stirring. The mixture was heated for 5 hours so that it boiled gently, the lower dark phase was separated off and the upper clear phase was poured into a receiver solution of 20 g of sodium carbonate and 20 g of sodium bicarbonate dissolved in 1 l of water. The mixture was stirred until cold, filtered off with suction and washed with water and little methanol. 18.5 g of pure dimethyl 5-nitro-isophthlate were obtained. By phase separation, the diIsobutyl ether was recovered almost completely from the mother liquor.

Example 8

220 ml of toluene and 80 ml of methanol were initially charged, 106 g of 5-nitro-isophthalic acid were added and 8 ml of concentrated sulfuric acid were added dropwise with heating. The mixture was heated at 80° C. for 8 hours, neutralized with 10% strength by weight of aqueous soda solution and stirred until cold. The mixture was filtered off with suction and the filter residue was washed three times with 100 ml each of 10% strength by weight of aqueous soda solution and then twice with water, and dried. 87.5 g of pure dimethyl 5-nitro-isophthalate were obtained.

Example 9 (for comparison)

At a temperature of 10° C., a mixture of 100 g of nitric acid and 302 g of sulfuric acid was added dropwise with stirring to a solution of 195 g of dimethyl isophthalate in 320 ml of 100% strength by weight of sulfuric acid and the mixture was stirred at 20 to 25° C. for another 3 hours. The mixture was then poured onto 1600 g of an ice/water mixture and the receiver solution was cooled in such a manner that the temperature did not exceed 10° C. Stirring was continued for 1 hour and the mixture was then filtered through an acid-proof filter. The product was washed free of acid using plenty of water and dried under reduced pressure.

230 g of product containing 98.0% by weight of dimethyl 5-nitro-isophthalate, 1.0% by weight of dimethyl 4-nitro-isophthalate and 0.3% by weight of monomethyl 5-nitro-isophthalic acid were obtained.

We claim:

1. A process for preparing di-$C_1$–$C_4$-alkyl 5-nitro-isophthalates, comprising the steps of:

dissolving or suspending 5-nitro-isophthalic acid in a mixture of a $C_1$–$C_4$-alkyl alcohol and a solvent which is immiscible or only partly miscible with water to form a reaction mixture, wherein 3 to 8 mol of the $C_1$–$C_4$-alkyl alcohol is used per mole of 5-nitro-isophthalic acid, heating the reaction mixture in the presence of a strong acid, and crystallizing formed di-$C_1$–$C_4$-alkyl 5-nitro-isophthalate from the reaction mixture.

2. The process of claim 1, wherein the heating step is performed for 4 to 5 hours.

3. The process as claimed in 1, wherein said $C_1$–$C_4$-alkyl alcohol is methanol.

4. The process as claimed in claim 1, wherein said $C_1$–$C_4$-alkyl alcohol is ethanol.

5. The process as claimed in claim 1, wherein the solvent which is immiscible or only partially miscible with water is an aromatic hydrocarbon, chloroaromatic ether or aliphatic ether.

6. The process as claimed in claim 1, wherein 0.2 to 5 parts by volume of the solvent which is immiscible or only partially miscible in water are employed, based on one part by volume of $C_1$–$C_4$-alkyl alcohol.

7. The process as claimed in claim 1, wherein the strong acids employed are sulfuric acid, hydrogen chloride (as a gas or as an aqueous solution), methanesulfonic acid, toluene-sulfonic acid or ion exchangers containing $HSO_3$ groups in an amount of 1 to 200% by weight, based on 5-nitro-isophthalic acid.

8. The process as claimed in claim 1, wherein the heating in the presence of a strong acid is carried out to temperatures in the range from 50 to 150° C.

9. The process as claimed in claim 1, wherein the heating step is performed between 2 and 20 hours.

10. The process as claimed in claim 1, wherein the entire reaction mixture or just the organic phase is treated with an aqueous solution of a base following the heating step.

11. The process as claimed in claim 1, wherein the organic phase is cooled prior to the crystallizing step to temperatures between 25 and 0° C.

12. The process as claimed in claim 1, wherein the organic phase is cooled prior to the crystallizing step to 20 to 25°C. and the mother liquor is then added to a subsequent reaction.

* * * * *

UNITED STATES PATENT AND TRADEMARK OFFICE
CERTIFICATE OF CORRECTION

PATENT NO.   : 6,002,041
DATED        : December 14, 1999
INVENTOR(S)  : Rauchschwalbe et al.

It is certified that error appears in the above-identified patent and that said Letters Patent is hereby corrected as shown below:

On the Title Page

In column 1, line 2, under "OTHER PUBLICATIONS", delete "paricular" and substitute --particular-- in its place.

In column 2, line 13, delete "(1996)" and substitute --(1966)-- in its place.

Signed and Sealed this

First Day of May, 2001

Attest:

NICHOLAS P. GODICI

Attesting Officer       Acting Director of the United States Patent and Trademark Office